United States Patent
Kilgus

(10) Patent No.: US 7,756,683 B2
(45) Date of Patent: Jul. 13, 2010

(54) MEASURING DEVICE AND METHOD FOR MEASURING AT LEAST ONE ENVIRONMENTAL PARAMETER

(75) Inventor: Traugott Kilgus, Mödling (AT)

(73) Assignee: MLU-Monitoring fuer Leben und Umwelt GES.m.b.H., Moedling (AT)

( * ) Notice: Subject to any disclaimer, the term of this patent is extended or adjusted under 35 U.S.C. 154(b) by 0 days.

(21) Appl. No.: 11/572,072

(22) PCT Filed: Jul. 8, 2005

(86) PCT No.: PCT/AT2005/000260

§ 371 (c)(1), (2), (4) Date: Jun. 19, 2007

(87) PCT Pub. No.: WO2006/005093

PCT Pub. Date: Jan. 19, 2006

(65) Prior Publication Data

US 2008/0040041 A1    Feb. 14, 2008

(30) Foreign Application Priority Data

Jul. 12, 2004  (AT) .............................. GM488/2004
Dec. 15, 2004  (AT) .............................. GM911/2004

(51) Int. Cl.
*G06F 11/00* (2006.01)

(52) U.S. Cl. ........................... 702/188; 702/189; 700/9; 700/10

(58) Field of Classification Search ................... 702/30, 702/32, 57, 64–65, 104, 130, 179, 188–189; 374/208

See application file for complete search history.

(56) References Cited

U.S. PATENT DOCUMENTS

| 3,477,955 A | * | 11/1969 | Hiltz | .............................. 252/4 |
| 4,818,348 A | | 4/1989 | Stetter et al. | |
| 5,381,950 A | * | 1/1995 | Aldridge | ...................... 236/1 R |
| 5,515,075 A | * | 5/1996 | Nakagiri et al. | .............. 345/111 |
| 5,801,297 A | | 9/1998 | Mifsud et al. | |
| 5,832,411 A | | 11/1998 | Schatzmann et al. | |
| 6,024,236 A | * | 2/2000 | Jannot et al. | ............... 220/4.02 |
| 6,205,803 B1 | * | 3/2001 | Scaringe | .................... 62/259.2 |
| 6,293,697 B1 | * | 9/2001 | Gul | ........................... 374/135 |
| 6,495,341 B1 | | 12/2002 | Zenhausern | |

(Continued)

FOREIGN PATENT DOCUMENTS

EP          0272774 B1 *  6/1988

*Primary Examiner*—Eliseo Ramos Feliciano
*Assistant Examiner*—Mi'schita' Henson
(74) *Attorney, Agent, or Firm*—Workman Nydegger

(57) ABSTRACT

A process for measuring at least one environmental parameter with at least one sensor (7.1, 7.2, ...), wherein environmental parameters detected by the sensor are converted into measured values of physical variables and are retrievable via a long-distance data connection, is characterized in that the environmental parameters detected by the sensor (7.1, 7.2, ...) are taken over in the form of voltage signals from a processor system of a data acquisition and processing unit (6) which calculates therefrom physical measured values in two steps while taking into account the progressions of calibration, stores said calculated measured values in database form along with the voltage signals, preferably making them available via a web server function, wherein, in a first step, voltage values which have been digitized and, possibly, have been preprocessed by statistical arithmetic operations are made available and, in a second step, the measured values are calculated therefrom (FIG. 1).

27 Claims, 2 Drawing Sheets

U.S. PATENT DOCUMENTS

| | | | |
|---|---|---|---|
| 6,560,543 B2 * | 5/2003 | Wolfe et al. | 702/22 |
| 7,093,453 B2 * | 8/2006 | Asan et al. | 62/186 |
| 2002/0062205 A1 * | 5/2002 | Roberts | 702/188 |
| 2002/0178789 A1 | 12/2002 | Sunshine et al. | |
| 2003/0154044 A1 * | 8/2003 | Lundstedt et al. | 702/104 |
| 2008/0121034 A1 * | 5/2008 | Lynam et al. | 73/335.05 |

* cited by examiner

MEASURING DEVICE AND METHOD FOR MEASURING AT LEAST ONE ENVIRONMENTAL PARAMETER

The invention relates to a process for measuring at least one environmental parameter with at least one sensor, wherein environmental parameters detected by the sensor are converted into measured values of physical variables and are retrievable via a long-distance data connection, as well as to a measuring device therefor.

BACKGROUND OF THE INVENTION

The pollution of the environment with harmful substances affects the quality of life and optionally also the health of persons staying in this environment and moreover has consequences with regard to the preservability of the respective flora and fauna. This realization results, on the one hand, in the necessity to develop processes for assessing the environmental quality parameters for relevant harmful substances and to employ said processes regularly and continuously, respectively, depending on a risk assessment in order to, on the one hand, monitor the observance of limiting values which are stipulated by laws or guidelines and, on the other hand, identify potentials for measures which allow the attainment of a target value. Thereby, it must be considered that the pollutant concentrations vary spatially and temporally.

Against this background, environmental quality monitoring networks have been established worldwide in the past 30 years which perform the required measurements using the available technology. The processes and assessment methods to be used for this purpose are standardized in detail for many areas of application, which, on the one hand, is indeed useful for the comparability of the assessment results but, on the other hand, inhibits the implementation of new processes and groundbreaking technology. In the field of air quality measurement, the measuring methods employed in the instruments have, for example, remained basically unchanged since the early 70ies.

The findings from the data obtained in said time period in comparison to medical data, i.e., the epidemiological research with respect to the impact of atmospheric pollutants, leads to the determination of limiting values and target values for the individual harmful substances. Thereby, it is necessary to distinguish between limiting values which must not be exceeded in the annual average and such values which must entail measures also in case of a short-term exceedance, i.e., alarm thresholds. Due to the technological advancement on the emitters' side (for example, by using catalytic converter technology or low thionated fuels) but also due to a shift in the composition of the parent population of all emitters (e.g., an increasing proportion of vehicles with Diesel drive units or a higher amount of solid biomass fuels), the focal points of the required assessments can shift over time, which is well displayed, on the one hand, by the decline in the significance of sulfur dioxide monitoring and, on the other hand, by the significant increase in the significance of an assessment of the concentration of fine dust (PM10). Thus, the respective monitoring systems must exhibit an appropriate flexibility in terms of the diversity of harmful substances to be detected.

In recent years, the attention of authorities in charge of preserving air quality has concentrated more and more on so-called "hot spots", i.e., areas in which, due to specific conditions such as a high concentration of emitters, specific meteorological positions or the like, limiting values and, occasionally, alarm thresholds are exceeded to an increased degree. Such areas can either be developed as permanent hot spots, for example, at extremely busy traffic junctions, or can arise temporarily, for example, during the implementation of large-scale building projects.

The prior art is characterized by a dichotomic situation:

On the one hand, automated measuring stations which measure with a high temporal resolution and detect a multitude of harmful substances are used. These stations usually consist of container-like air-conditioned buildings or constructions which protect the laboratory equipment installed in their interior (per harmful substance, there is typically one analytical instrument comprising a mains supply, a sensor, signal processing, internal measured-value calculation, a display and an operating element as well as interfaces for communication with a master computer) from the elements and from access by unqualified persons. Appropriate sampling systems conforming to standards as well as instruments for the temporally synchronized detection of meteorological data (rain, temperature, wind force and direction) complete the measuring setup. Typically, such a station also contains a local data acquisition unit (front-end processor, logger or the like) which then transfers the measured values via long-distance data transmission to the centre of the measuring network where the analysis is performed using specialized software. As can be understood from the above description, these stations are complex installations which, due to their dimensions and the supply systems required for the operation as well as the investments associated therewith, typically cover areas of several to several hundred square kilometres per station and thus are unsuitable for the—at best temporary—use at a plurality of hot spots.

On the other hand, there are passive or diffusion collectors functioning according to Fick's law of diffusion which are limited in terms of the detected number of different harmful substances according to the number and type of the diffusion collectors installed per collecting point, wherein a single diffusion collector is typically suitable only for one harmful substance while, however, in specific cases, up to three harmful substances can be detected simultaneously. Therefore, as a result of the small size of the individual collectors—typically, they are small tubes having a maximum length of several 100 mm and a diameter of typically 10-20 mm—a measuring arrangement comprising 4 diffusion collectors of this kind corresponds, with regard to its size, to typical nest boxes for singing birds and, in terms of the compactness of the dimensions, is thus suitable for locally highly resolved measurements. However, the typical averaging time, i.e., the time span for which an individual measured value can be determined, is 7 to 14 days for all diffusion collectors. Since, in addition, said collectors must also be taken to a laboratory for analysis and must be evaluated there by desorption and further analysis methods, assessments of the pollutant concentration in the measuring range cannot be provided in real time. During the measurement, there is also no detection of local meteorological conditions.

Self-sufficient analyzers are used in the conventional technology. This has historical as well as practical reasons. The historical reasons lie in the ongoing development of analyzers for the harmful substances which are relevant at a particular time.

Each new harmful substance has been given a new analyzer which, in turn, has been added to a measurement rack in order to be able to measure a new harmful substance in the measuring station.

Normally, such analyzers measure only one harmful substance per analyzer. This has also a historical background which is basically accounted for by the performance of the electronics. A typical 19" measuring instrument was filled to capacity by the required electronic components with regard to measurement and control technology as well as the power supply unit, the pump and the actual measuring sensor, the display and the control device. In spite of that, the devices were extremely sensitive to variations in temperature and air humidity, which is typical of laboratory equipment. Therefore, the devices were integrated in air-conditioned measurement rooms.

Still today, the standards for air quality systems are based on this architecture.

Thus, in the normal case, each analyzer for gaseous atmospheric pollutants consists of sample ducts internal to the measuring device which receive the sample material (test gas) from a central sampling, which, in turn, is specified in terms of shape, size and design according to standards, and, first of all, convey the same to a particle filter which protects the usually optical measuring systems from soiling by filtering out dust. Thereupon, the duct leads to a sensor. The actual measurement principles of the sensor are physical in nature and have remained unchanged for decades. They are also laid down in the standard as so-called reference methods.

In a measuring station which, due to the necessary manual interventions, must be designed such that said interventions can be carried out in accordance with safety regulations and that the analyzers are protected from unauthorized outside access, all analyzers in at least one measurement rack are usually mounted on top of each other in an assembly form as common in the industrial process technology. All devices are supplied via a switch cabinet embedded in the measuring station.

The analyzers are designed for set-up in interior spaces and react to variations in ambient conditions (air temperature and humidity) mostly with measured value variations, in case of more extreme deviations also with an equipment failure.

In order to maintain the quality of the measurement, the room temperature and air humidity must therefore be kept within particular variation ranges at the known measuring stations. For this purpose, an air volume resulting from the dimension of the station is used on the one hand, which air volume serves as a thermal mass and keeps the same, in terms of the key data air temperature and humidity, within the range which is required for the desired measuring accuracy, using an appropriately dimensioned conventional air-conditioning system.

It is known that the power required for a proper operation of the measuring system thereby depends on the size of the modified volume, the heat transition values of the boundary walls, the outside conditions as well as the number and capacity of consumers producing waste heat. The latter consist, on the one hand, of the waste heat of auxiliary units such as power transformers, pumps and the like and, on the other hand, of specific sources of waste heat such as, for example, infrared emitters or heated catalysts, which result from the applied measuring methods.

For common measuring stations corresponding to the prior art, the requirement of energy typically amounts to several kW as a result of the installation sizes and the high number of sources of waste heat so that, usually, power supply terminals must also be provided for the operation.

A central sampling unit comprising a main pump provides for an adequate flow of test material from which the analyzers in turn withdraw their test gas.

Normally, data pooling is effected by means of a data logger with an integral microprocessor which requests the data as a master from the measuring instruments and stores them appropriately along with a time value. Thereby, only fully calculated measured values of the individual analyzers are available for storage. In some embodiments, a spreadsheet with zero and span information which allows an assessment of measuring results can be filed in addition. Today, most data loggers are provided with local mass storage such as, e.g., a hard disk on which the queried measured value tables can be stored temporarily.

Via a modem, said tables are then sent via long-distance data transmission to a master computer in the measuring centre according to a preprogrammed (time-dependent) pattern. Normally, the statistical evaluation, e.g., in daily average values or the like, is conducted there and is made available to the public from there. It can also be made available to the public by transmission to a web server.

DETAILED DESCRIPTION

Figure 1:
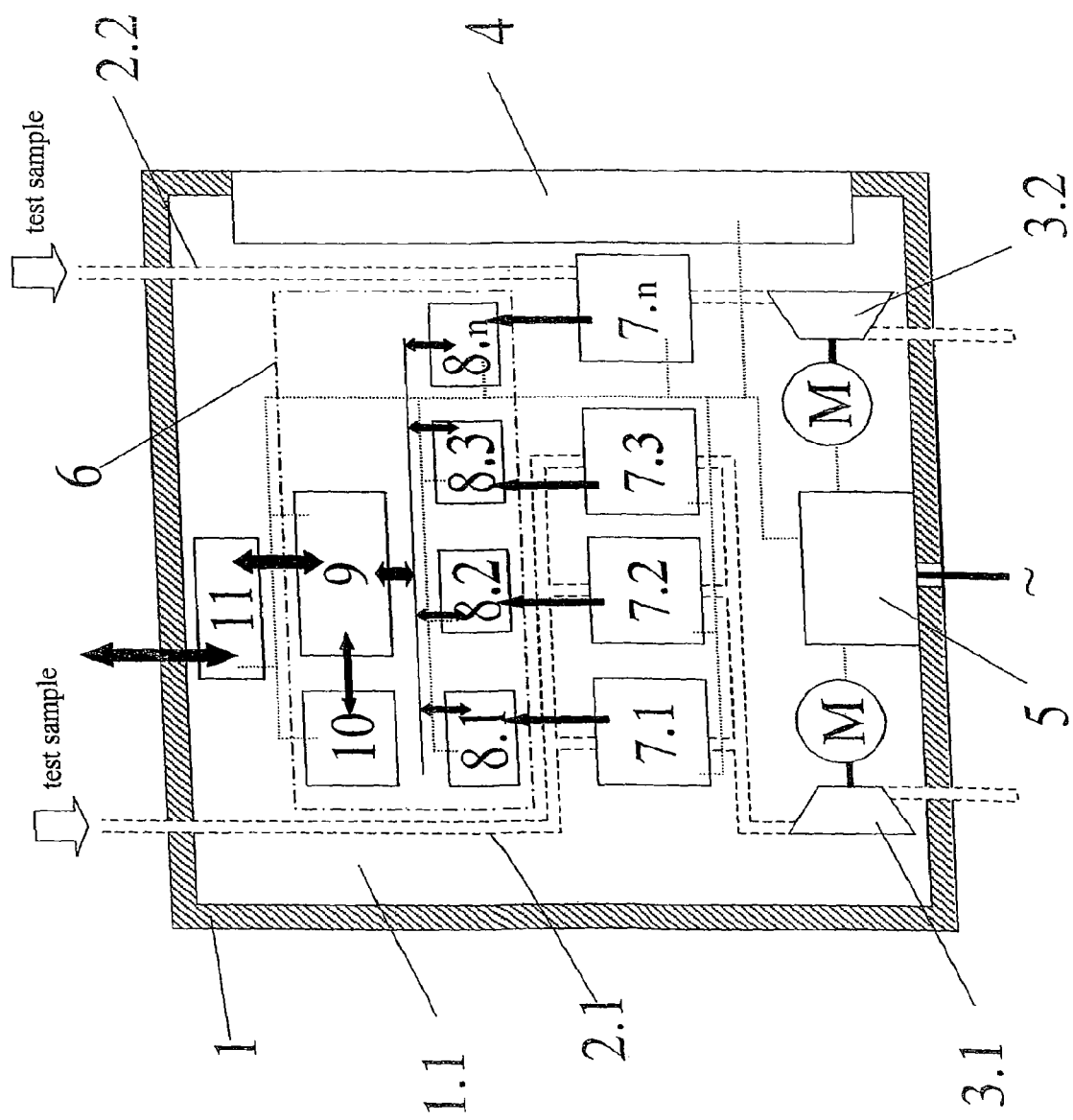
FIG. 1 illustrates a measuring device for measuring environmental parameters according to a first embodiment of the invention.

The invention aims at avoiding the above-described difficulties and disadvantages of measuring devices according to the prior art and has as its object to provide a process of the initially described kind which enables the design of a measuring device in a highly compact and, if need be, portable manner, wherein variations in ambient conditions may cause no or only insignificant variations in measured values. In particular, a measuring device according to the invention is also supposed to be able to function as a data evaluation station, and, furthermore, transparency is to be provided between the raw signal, i.e., the voltage signal, and the physical measured values resulting therefrom. Apart from a minimization of the required space, e.g. the base area, a reduction in the supply requirements, e.g., the current demand, is also an essential objective of the invention.

With a process of the initially described kind, said object is achieved in that the environmental parameters detected by the sensor are taken over in the form of voltage signals from a processor system of a data acquisition and processing unit which calculates therefrom physical measured values in two steps while taking into account the progressions of calibration, stores said calculated measured values in database form along with the voltage signals, preferably making them available via a web server function, wherein, in a first step, voltage values which have been digitized and, possibly, have been preprocessed by statistical arithmetic operations are made available and, in a second step, the measured values are calculated therefrom.

Advantageous variants of said process are included in subclaims 2 to 5.

A measuring device for measuring at least one environmental parameter according to the process according to the invention, comprising a closed casing, a central current supply and at least one sampling unit with an associated pump and at least one sensor, for solving the problem underlying the invention is characterized by a data acquisition and processing unit having a modular design and comprising at least one signal processor for receiving the measuring signals of at least one sensor and converting them into voltage values, wherein the signal processor is coupled to a central processor for converting the voltage values into measured values of physical variables, which central processor, in turn, is coupled to a local memory of measured values.

Advantageous advanced embodiments of such a measuring device are included in subclaims 7 to 31.

Below, the invention is illustrated in further detail by way of two exemplary embodiments which are schematically depicted in the drawing in a block diagram illustration.

According to FIG. 1, a compact measuring device for measuring environmental parameters is made up of the following elements: a compact weatherproof and thermally insulating casing 1 made of metal or plastic and comprising two sampling lines 2.1, 2.2 and the associated pumps 3.1, 3.2 as well as an integral device 4 for air-conditioning the interior 1.1 of the casing and the central current supply 5. The data acquisition and processing unit 6 having a modular design is embedded therein as a core functional element, wherein, in the first processing level, an architecture with distributed processors is used, with the measuring signals of each sensor $7.1 \ldots 7.n$ used in the system being guided to a separate signal processor $8.1 \ldots 8.n$. The conversion into digital values and a possible statistical evaluation, e.g., averaging, which is required for the application or is reasonable, take place there. At the output of the signal processor, a digitized voltage value of the sensor, which value has possibly been evaluated, is present which is converted in the central processor 9 into measured values provided with physical variables, for example concentrations, and can subsequently be stored on a local mass storage device 10 or provides data for long-distance data transmission 11 via the necessary interfaces to different embodiments. Since the central processor 9 also possesses web server functionality, the supply of data for the user is effected via browser software so that the measured data can be requested from every computer with internet browser and connection without any special software.

The second sampling is needed only if a measurement of fine dust is desired. In this case, the sampling is an essential part of the measuring process since it is designed as a sharp-edged separator and thus only particles corresponding to a particular diameter classification are separated. All gaseous pollutants are measured with a single sampling.

The system can be configured and enlarged differently depending on the respective measuring task. The configuration is effected by the addition or replacement, respectively, of sensors and the first signal processing level associated therewith. Typical configurations of exemplary applications are:

Means for classical immission or emission measurement comprise one to five sensors, wherein different measuring methods (for example, non dispersive infrared sensors for carbon monoxide and dioxide, respectively, chemiluminescence for nitric oxides, UV photometry for ozone, UV fluorescence for sulfur dioxide, hydrogen sulfide and similar sulfur compounds, and also non dispersive UV absorption for nitric oxides as well as PID sensors for volatile organic substances or FID sensors for determination of hydrocarbon concentrations) are used in this case. In addition, a sensor for measuring fine dust and particle concentration, respectively, is typically integrated, with a further sampling being required for said sensor.

Particular applications consist in means for qualitative monitoring which use, for example, arrays of semiconductor sensors made, for instance, of metallic oxide.

In a further embodiment, the sensors for gathering relevant meteorological data such as, for example, wind velocity and direction or air pressure and temperature as well as air humidity can be embedded in the system by the attachment or incorporation, respectively, of sensors.

In another embodiment, for example for applications in the field of traffic, a sensor for the detection of noise parameters such as acoustic pressure can be embedded in the system.

In a particularly advantageous embodiment for measuring air quality, the invention is integrated into an advertising pillar, which, at best, is capable of being backlit, or into a large-scale display in such a manner that both the advertising and the measuring functions are ensured.

In a further advantageous embodiment for application as a means for monitoring pollutant concentrations in fluids, especially but not exclusively water, sensors for determining the contents of nitrates, phosphates, the Total Organic Content (TOC), pH-value or the biological oxygen demand (BSB) and similar measured variables are, for example, used. Said sensors function primarily according to electrochemical methods, employ ion-selective membranes or utilize redox effects. Photometric sensors or sensors which make use of the fluid's electrical conductivity as a measuring method are common as well. In the field of TOC, measuring methods comprising the decomposition of organic substances via high-temperature oxidation or the addition of reagents such as boric acid and the measurement of the $CO_2$ concentration thus forming are primarily used.

Figure 2:
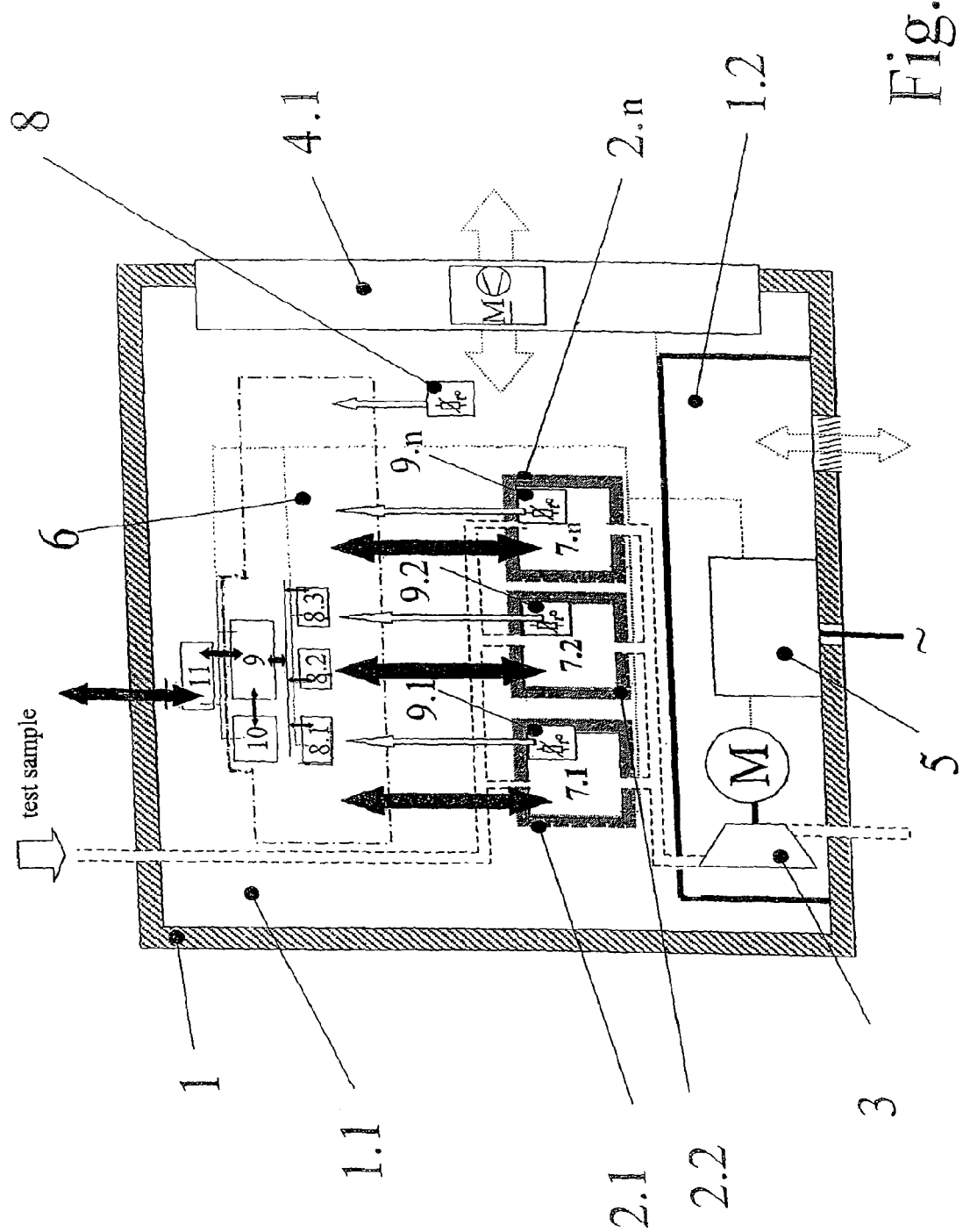
FIG. 2 illustrates another embodiment of a measuring device according to the invention.

FIG. 2 shows an embodiment of the invention having a minimized expenditure of auxiliary energy. The measuring device according to FIG. 2 comprises a thermally insulating casing 1 made of metal or plastic, wherein the interior of the casing is divided, for an improved thermal management, into at least two partial spaces, namely the measurement room 1.1 comprising sensors $7.1 \ldots 7.n$ as well as the data processing unit 6 and the separately ventilated supply room 1.2 comprising at least one sampling pump 3 and at least one current supply 5 and a mains supply unit, respectively, and wherein the sensors $7.1 \ldots 7.n$ arranged in the measurement room 1.1 and the components which are relevant for the thermal management such as, for example, heated catalysts are thermally shielded once more from the sensors by individually adapted insulating elements 2.1 to 2.n and wherein, in the associated modularly designed data acquisition and processing unit 6, an electronic climate control of the measuring conditions in the measurement room conducted according to the measured values of a temperature sensor 8 mounted in the measurement room and a monitoring of the operating temperatures of the measuring sensors or of their separately insulated components are effected via temperature sensors $9.1 \ldots 9.n$, whereby a shutdown is triggered if the admissible operating temperatures of the thermally insulating components are exceeded.

Depending on the type, configuration and number, respectively, of the measuring sensors $7.1 \ldots 7.n$, cooling is effected either via a conventional compression air conditioning system 4 attached to an outer wall of the casing or via a cooling unit 4.1 consisting of at least one Peltier element and a forced ventilation system, which cooling unit is installed in the same place.

The temperature control thus implemented allows the operation of the compact means for measuring environmental parameters without any significant losses in measuring accuracy but with connected electrical loads which, typically, account for only 10% of the typical demand of conventional measuring stations and, in any case, remain below 0.5 kW and hence can always be implemented by means of a single-phase power supply.

The invention provides the following advantages over the prior art:
1. omission of a number of redundant components which, however, become truly visible only in comparison to a station comprising more than one sensor. Thus, the measuring device according to the invention operates with only one power supply unit for all sensors and requires no displays and operating units. Several or all sensors, respectively, for gaseous pollutants are operated via a common pump. In this way, a previously unachievable compactness and minimization, respectively, of the space required for the measuring device can be achieved.

2. The thermal management of the system is designed for a minimum of heat emission of the individual elements and, hence, the need for air conditioning and the expenditure of energy necessary therefor, respectively, are significantly reduced.

3. In a conventional analyzer, the digitized analog signal is completely processed in the measuring device and is output as a finished measured value. The system is thereby closed, access from the outside to the "internal values", which result in the individual measured values, is impossible. According to the invention, a distributed processor system is used. The analog-to-digital conversion is performed in an integral microcontroller (first processor level) and—if requested accordingly by the higher-order system computer (second processor level)—a first statistical evaluation, e.g., averaging, of the digitized voltage signals is also performed immediately. The status signals and the set/actual values of the individual local-mode measuring conditions—which, in turn, are or can be, respectively, identical to those of conventional analyzers since, due to the regulations of the standard with regard to reference methods, besides other types, the identical sensors must also be "operated" such as in conventional analyzers—are transferred from the sensor control level (first processor level), which is also controlled by a microcontroller, to the higher-order system computer, also via the bus which is inherent to the device. In contrast to conventional analyzers, however, this sensor control level is not defined exclusively for one sensor but is able to supply a plurality of sensors including electrochemical sensors or semiconductor sensors. Using the information from the first processor level, the conversions into physical measured values are then performed in the second processor level on the basis of the calibration data. All data jointly reside in a real-time database. In this way, a presently unique transparency from the raw signal of the sensor, the marginal conditions of the measurement (global parameters and status parameters of the measuring instrument) to the finished measured value is achieved. The database is then accessible in various forms, e.g. via a web server. A normal user can view the data in an appropriate form deposited in the system, advanced users are allowed to download or transfer certain data to a server where they can be integrated into a monitoring system along with other measured values such as those of a conventional station. Advanced user or service personnel have access to the complete database in real time at any point of time from every computer in the world—but also from every web-enabled mobile phone or PDA—and are thus able to check the function of the system such as, for example but not exclusively, lamp voltages or ventilator speeds. Moreover, by transmission of data files, individual parameters can be actively varied or even complete software elements can be replaced, which otherwise have a typical firmware character in the devices. Furthermore, thanks to the web server function, the system can also transfer alarm or other status messages via conventional web-based functions such as, e.g., e-mail in order to thus enable, if need be, a replacement even before a breakdown of a component renders invalid the measured values. Access to the outside world, particularly the internet, is thereby effected of course in a conventional manner, i.e., via modem, radio communication/GSM/GPRS/UMTS or W-LAN connection, since, otherwise, connection to the internet is impossible.

4. In contrast to all other systems which currently are used in this field, no manufacturer-specific software—not even a so-called driver—is required for communication with the measuring device according to the invention, only one of the web browsers installed as standard software (MS Internet Explorer, Netscape Navigator, Mozilla, etc.) has to run and it is necessary to know the internet address of the device and to have the password which is required for the desired privileges.

In total, this leads to a miniaturization factor of approx. 10 compared to the smallest known station suitable for multiple components and designed in a conventional architecture and to a miniaturization factor of approx. 100 compared to the so-called complete stations. The energy consumption decreases from typically 3500 W and thus a three-phase current (rotary current) to typically 350 W for the measurement of three pollutant components and thus clearly to a single-phase current with the potential for a mobile network-independent current supply. However, the quality of the measurement remains comparable to that of conventional complete stations.

What is claimed is:

1. A measuring device for measuring at least one environmental parameter, the measuring device comprising:
   a closed, thermally insulating casing;
   a central current supply;
   at least one sampling unit with an associated pump and one or more sensors;
   a data acquisition and processing unit having at least one signal processor for receiving the voltage signals of the at least one sensor and converting the voltage signals into voltage values, wherein the signal processor is coupled to a central processor for converting the voltage values into measured values of physical variables;
   a database including stored measured values of physical variables received from the data acquisition and processing unit;
   a long distance data transmission unit configured to retrieve measured values from the database and transmit the measured values over a long distance data connection; and
   wherein an interior of the casing is divided, in terms of thermal control, into a force-ventilated supply room housing the central current supply and a measurement room housing the one or more sensors and one or more subcomponents emitting waste heat, the measurement room provided with controlled measuring conditions and wherein the one or more sensors are thermally shielded individually from the measurement room via thermal insulation.

2. A measuring device according to claim 1, wherein a compression air conditioning system is included as an active cooling means.

3. A measuring device according to claim 1, wherein at least one force-ventilated Peltier element is included as an active cooling means.

4. A measuring device according to claim 1, wherein the temperature of the components beneath the insulations can be monitored in terms of their temperature by means of temperature sensors.

5. A measuring device according to claim 1, wherein in case the admissible operating temperature of the sensors or sensor components, respectively, beneath the individual insulations is persistently exceeded, the sensors or sensor components can be switched off via the central data acquisition and processing unit.

6. A measuring device according to claim 1, further comprising subunits operating according to common physical measuring methods selected from a group consisting of NDIR, NDUV, PID, FID, chemiluminescence, and UV absorption are included as sensors for the determination of gas concentrations.

7. A measuring device according to claim 1, further comprising subunits operating according to the electrochemical principle with zirconium oxide or according to the paramagnetic principle are included as sensors for measuring the oxygen concentration in gases.

8. A measuring device according to claim 1, wherein subunits composed of at least one semiconductor sensor are included as sensors for the determination of gas concentrations.

9. A measuring device according to claim 1, wherein subunits composed according to the electrochemical principle are included as sensors for the determination of gas concentrations.

10. A measuring device according to claim 1, wherein one additional subunit is provided for measuring the particle concentration in gases by means of known methods selected from the group consisting of microbalance, light scattering, and absorbance.

11. A measuring device according to claim 1, comprising additional sensors for wind velocity, wind direction, air temperature, air pressure and air humidity, wherein said additional sensors are embedded in the system.

12. A measuring device according to claim 1, wherein one additional subunit is provided for the measurements of noise parameters including acoustic pressure.

13. A measuring device according to claim 1, wherein sensors for determining the contents of harmful substances in fluids are provided as subunits which operate according to coulometric methods.

14. A measuring device according to claim 1, wherein sensors for determining the contents of harmful substances in fluids are included as subunits which operate according to electrochemical methods, using in particular also ion-selective membranes.

15. A measuring device according to claim 1, wherein sensors for determining the contents of harmful substances in fluids are included as subunits which operate by determining the electrical conductivity.

16. A measuring device according to claim 1, wherein sensors for determining the contents of harmful substances in fluids are included as subunits which operate according to photometric methods.

17. A measuring device according to claim 1, wherein sensors for determining the contents of harmful substances in fluids are included as subunits which determine the TOC (Total Organic Compounds) content via methods of decomposing organic substances by conversion into carbon dioxide, applying at least one of a high-temperature treatment and using chemical reagents.

18. A measuring device according to claim 1, wherein at least one sensor for determining the pH-value of fluids is included.

19. A measuring device according to claim 1, wherein at least one sensor for determining the BSB (biological oxygen demand) of fluids is included.

20. A measuring device according to claim 1, wherein the measuring device is integrated into a public facility, wherein the public facility comprises an advertising medium.

21. The measuring device of claim 17, wherein the chemical reagent comprises boric acid.

22. The measuring device of claim 20, wherein the advertising medium includes at least one of an advertising pillar, a large-scale display, into a telephone box, and a bus stop.

23. A measuring device according to claim 1, wherein the subcomponent emitting waste heat includes a heated catalyst.

24. A measuring device according to claim 1, wherein an interface for a long-distance data transmission unit is associated to the central processor.

25. A measuring device according to claim 1, wherein the central processor has a web server function.

26. A measuring device according to claim 1, wherein at least one controlled Peltier element mounted to an outer wall of the casing is included as a temperature control means.

27. A measuring device according to claim 1, wherein a micro air conditioning system embedded in the outer wall of the casing is used as a device for temperature control.

* * * * *